US00PP33544P2

(12) United States Plant Patent
Jimenez et al.

(10) Patent No.: US PP33,544 P2
(45) Date of Patent: Oct. 12, 2021

(54) PINEAPPLE PLANT NAMED 'VINTAGE RUBY'

(50) Latin Name: *Ananas comosus*
Varietal Denomination: Vintage Ruby

(71) Applicant: Del Monte International GmbH, Monaco (MC)

(72) Inventors: Mario Jimenez, Cartago (CR); Gerardo Matarrita, San Jose (CR); Freddy Vargas, Alajuela (CR); Hans Sauter, Miami, FL (US)

(73) Assignee: DEL MONTE INTERNATIONAL GMBH, Monte Carlo (MC)

( * ) Notice: Subject to any disclaimer, the term of this patent is extended or adjusted under 35 U.S.C. 154(b) by 0 days.

(21) Appl. No.: 16/873,912

(22) Filed: Aug. 11, 2020

(51) Int. Cl.
*A01H 5/08* (2018.01)
*A01H 6/22* (2018.01)

(52) U.S. Cl.
USPC ..... Plt./156

(58) Field of Classification Search
USPC ..... Plt./156
See application file for complete search history.

*Primary Examiner* — Susan McCormick Ewoldt
*Assistant Examiner* — Karen M Redden
(74) *Attorney, Agent, or Firm* — Dickinson Wright PLLC; Kristopher Lance Anderson

(57) ABSTRACT

A new and distinct pineapple plant named 'Vintage Ruby', comprising certain unique traits, including color of the fruit's shell at the immature state that is deep dark purple, and at the mature state is bright reddish/purple.

6 Drawing Sheets

Genus and species: *Ananas comosus.*

Figure 1:
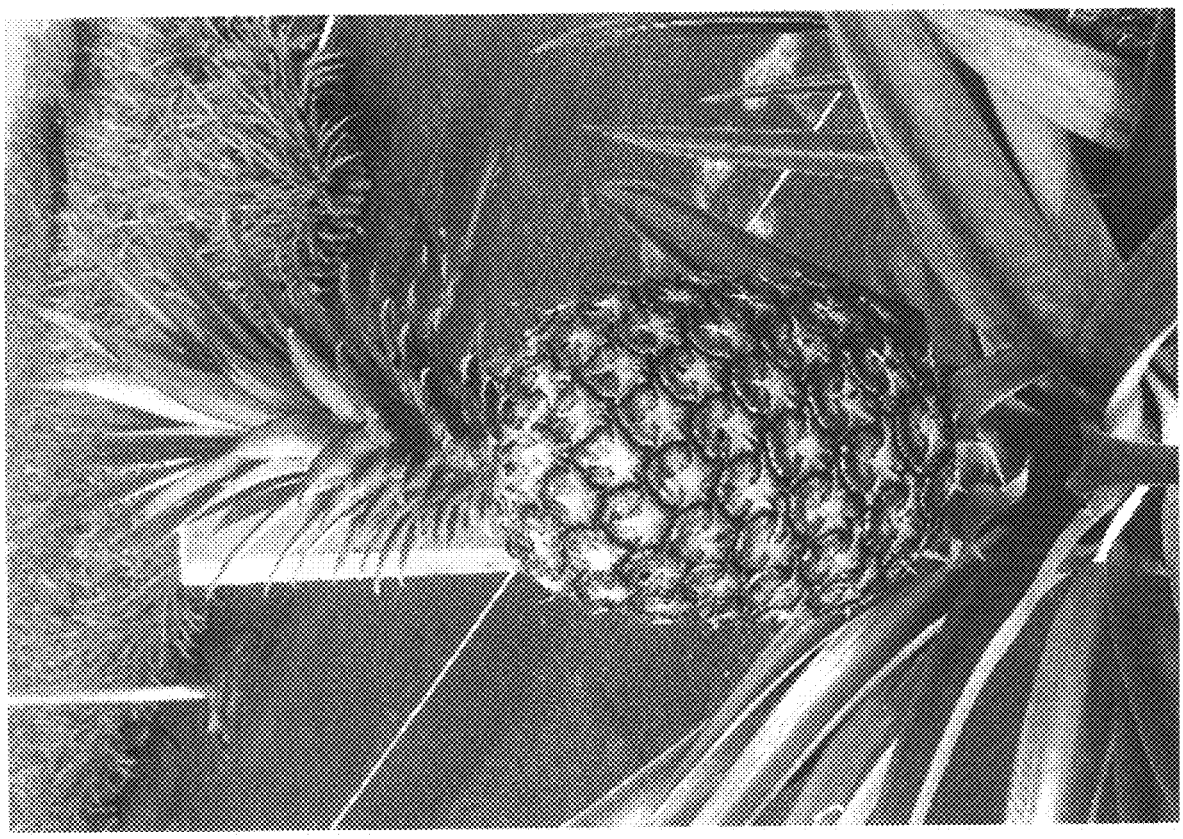

Variety denomination: 'VINTAGE RUBY'.

This application includes material that is subject to copyright protection. The copyright owner has no objection to the facsimile reproduction by anyone of the patent disclosure, as it appears in the Patent and Trademark Office files or records, but otherwise reserves all copyright rights whatsoever.

BACKGROUND OF THE NEW PLANT

The present invention comprises a new and distinct pineapple variety of *Ananas comosus*, hereinafter referred to as the variety named 'Vintage Ruby'. The variety has been developed by sexual crossing between plants, selected by mass selection of the hybrids. The process started during the year 2008, using the variety *A. comosus* var. *comosus* 'Morada' cultivar (non-patented) as parent, brought from Kunia, Hi. This plant was crossed with the variety 'MD-2' (non-patented), commercially known as 'Del Monte Gold'. The pineapple plant 'Vintage Ruby' was developed through sexual hybridization (hand-pollination) at Buenos Aires, Puntarenas, Costa Rica. The development process took eleven consecutive years of hybridization, planting and selection. The new variety 'Vintage Ruby' was the final result of a back-cross of one selected plant of the F1, with a selected plant of 'MD-2', to achieve the combination of characters of interest to consider 'Vintage Ruby' as a variety of commercial potential.

The main objective of the hybridization program was to obtain a pineapple plant with an attractive fruit in shape and size, plus excellent organoleptic traits that satisfy market requirements. Finally, the new cultivar was developed for the purpose of seeking a red or dark purple fruit shell, characteristic that distinguish it from its parental materials.

The new cultivar was effectively asexually reproduced true-to-type at Buenos Aires, Puntarenas, Costa Rica via leaf crown budding technique.

SUMMARY OF THE INVENTION

The invention is related to a new and distinct pineapple variety of the Bromeliaceae family, which was derived from a backcross (BC) between the 'MD-2' and the F1 ('MD-2' X 'Morada' cultivar), through hand-pollination and mass selection process during eleven years.

The selected hybrid is distinct in most characteristics to the 'MD-2' parent and was more alike to the F1 parent. The color of the fruit's shell at the immature state is deep dark purple, and at the mature state is bright reddish/purple. The selected backcross 1 (BC1) plant's fruit has an internal quality and pulp color similar to the 'MD-2' fruit. The total soluble solid contents (TSS), citric acid, ascorbic acid, pulp color, and the size of the fruit are similar to the 'MD-2'. The fruit is cylindrical to slightly conical in shape, has a very pleasant aroma, and delectable taste, similar to the 'MD-2'. One important trait is that it exhibits the hybrid vigor, producing higher yields in comparison to its F1 parent.

The new variety is characterized by purple/brownish color in the leaves, smooth with occasional presence of spines at the tip. Leaf color is similar, but not equal to the F1 and to the original 'Morada' cultivar, contrasting to 'MD-2'.

This plant does not produce slips unlike its parents, which do always produce at least one (See FIG. 1).

BRIEF DESCRIPTION OF THE PHOTOGRAPHS

The accompanying pictures illustrate the overall appearance of the new *Ananas comosus* var. *comosus* 'Vintage Ruby' showing the colors as reasonably possible with colored reproductions of this type. Colors in the photographs may differ slightly from the color values cited in the detailed botanical description, which accurately described the colors of 'Vintage Ruby'.

FIG. 1. View of the new variety 'Vintage Ruby' at 13.5 months (date of planting (DP) to date of forcing (DoF)=8 months+5.5 months after forcing (MAF)) showing the absence of slips.

Figure 2:
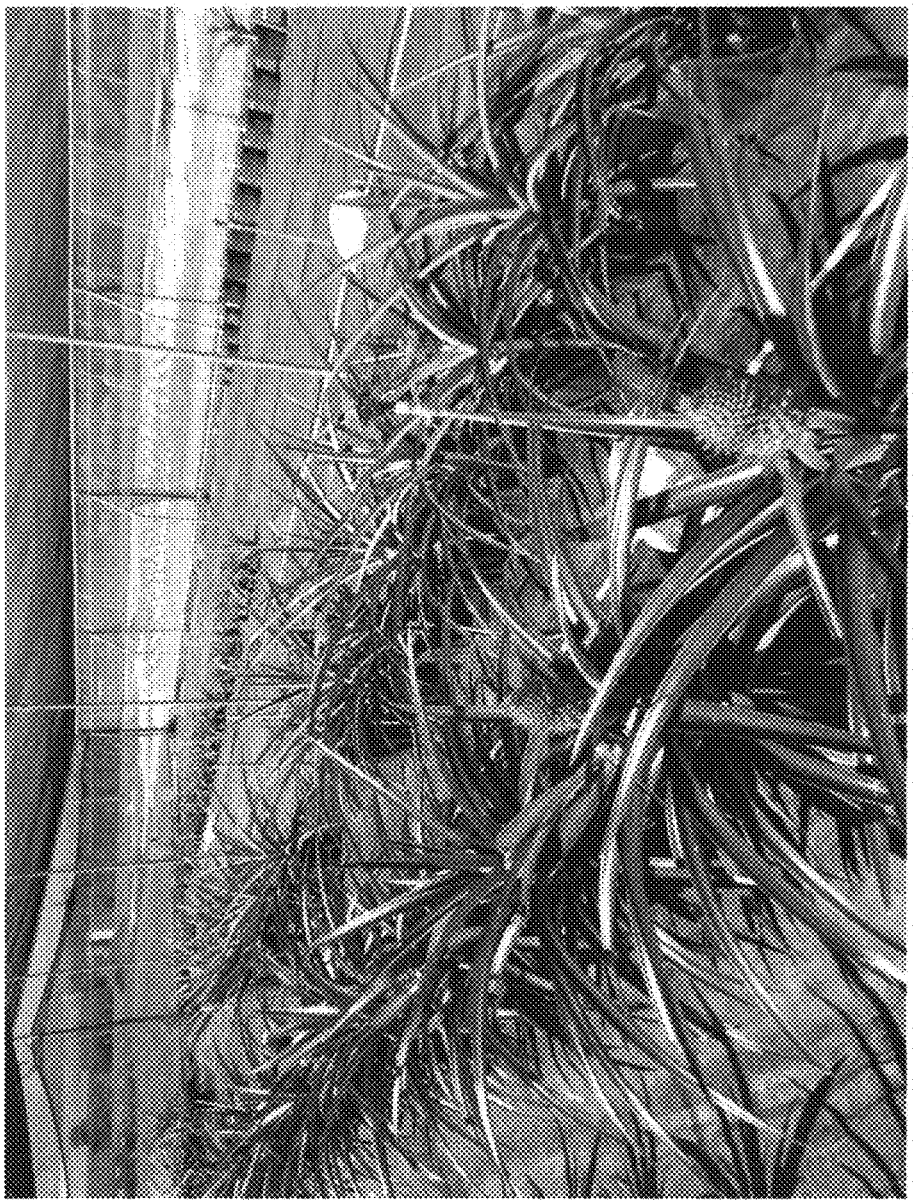

FIG. 2. View of a group of plants 'Vintage Ruby' at 10.5 months (DP to DoF=8 months+2.5 MAF).

Figure 3:
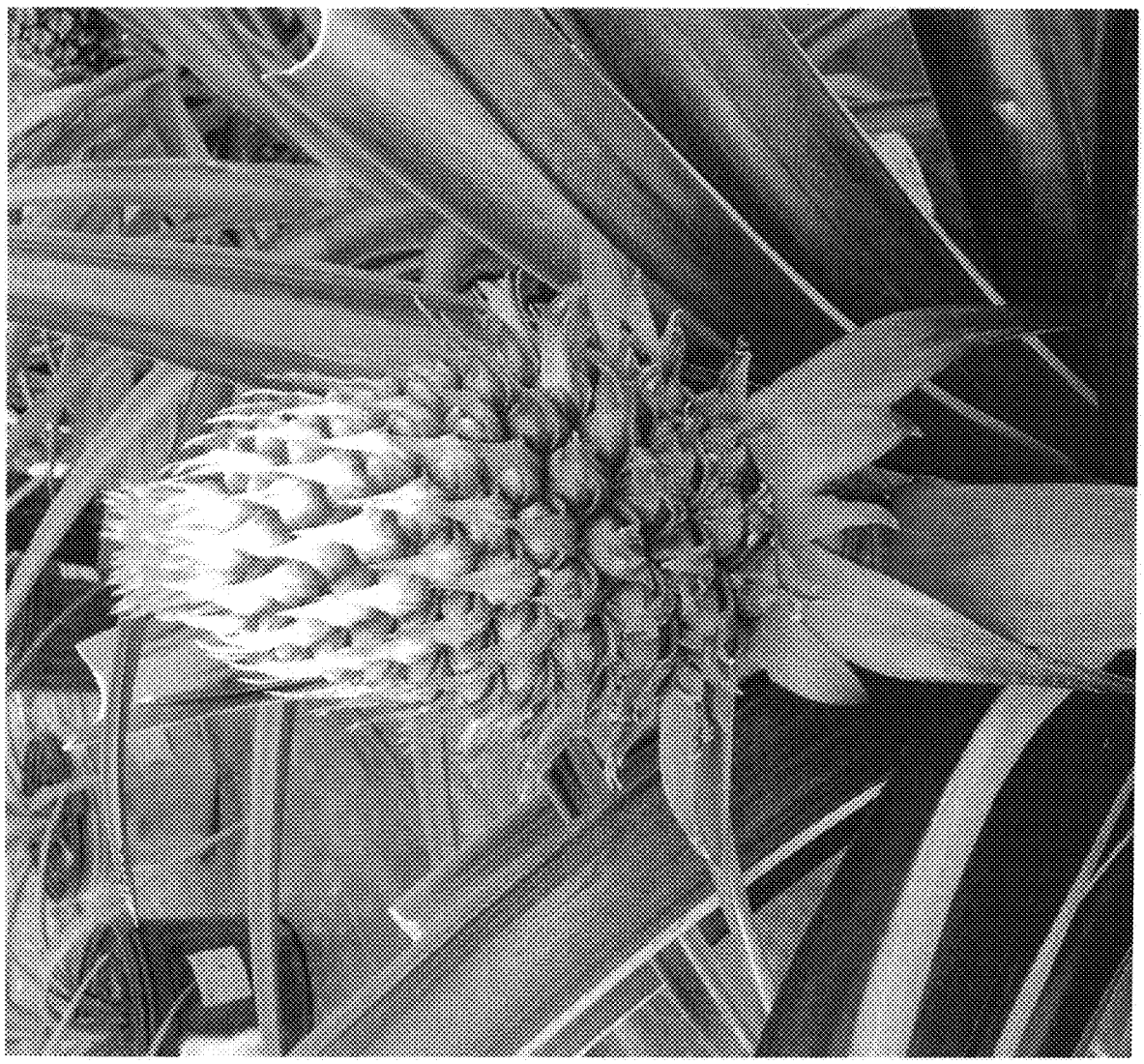

FIG. 3. Side view of inflorescence of 'Vintage Ruby' at 10.5 months (DP to DoF=8 months+2.5 MAF).

Figure 4:
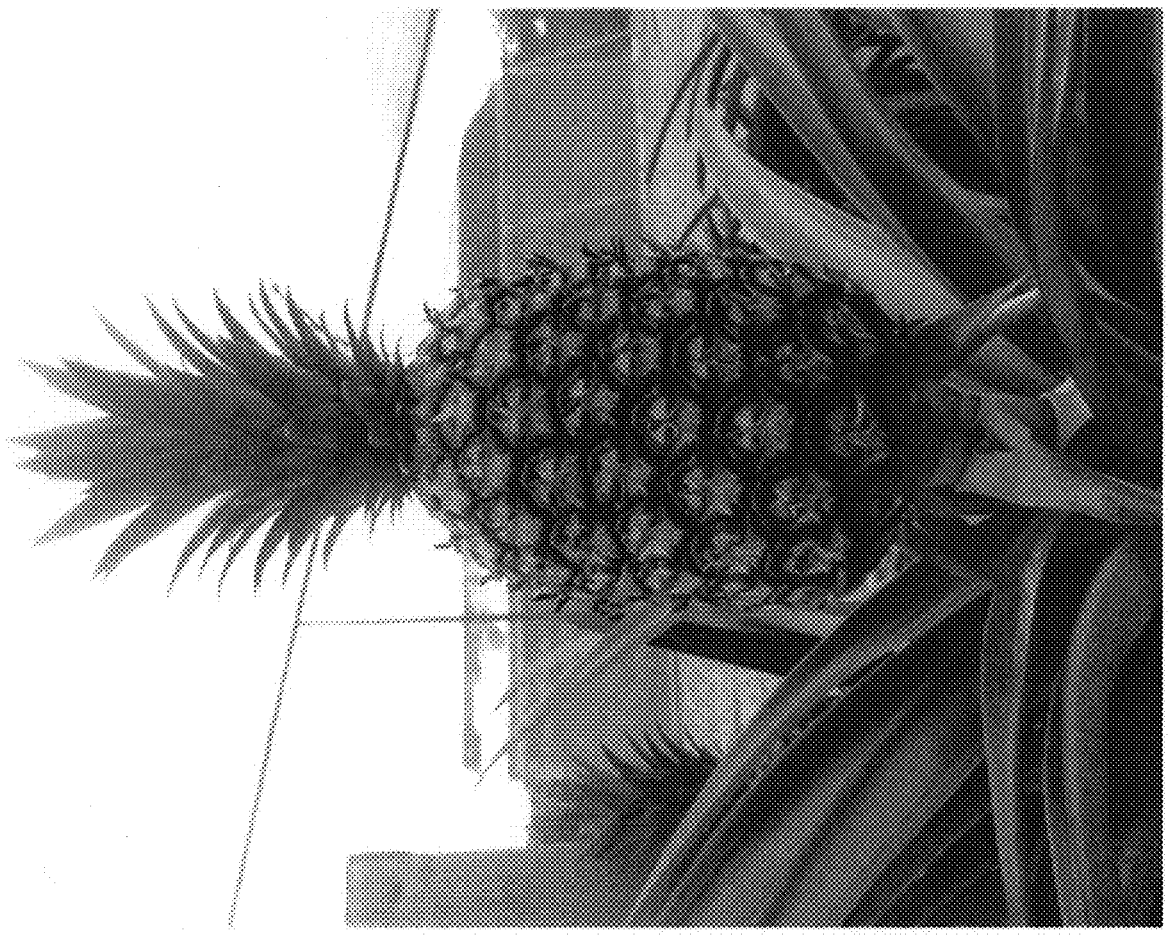

FIG. 4. Shows a close-up of an immature fruit 'Vintage Ruby' at 11.3 months (DP to DoF=8 months+3.3 MAF).

Figure 5:
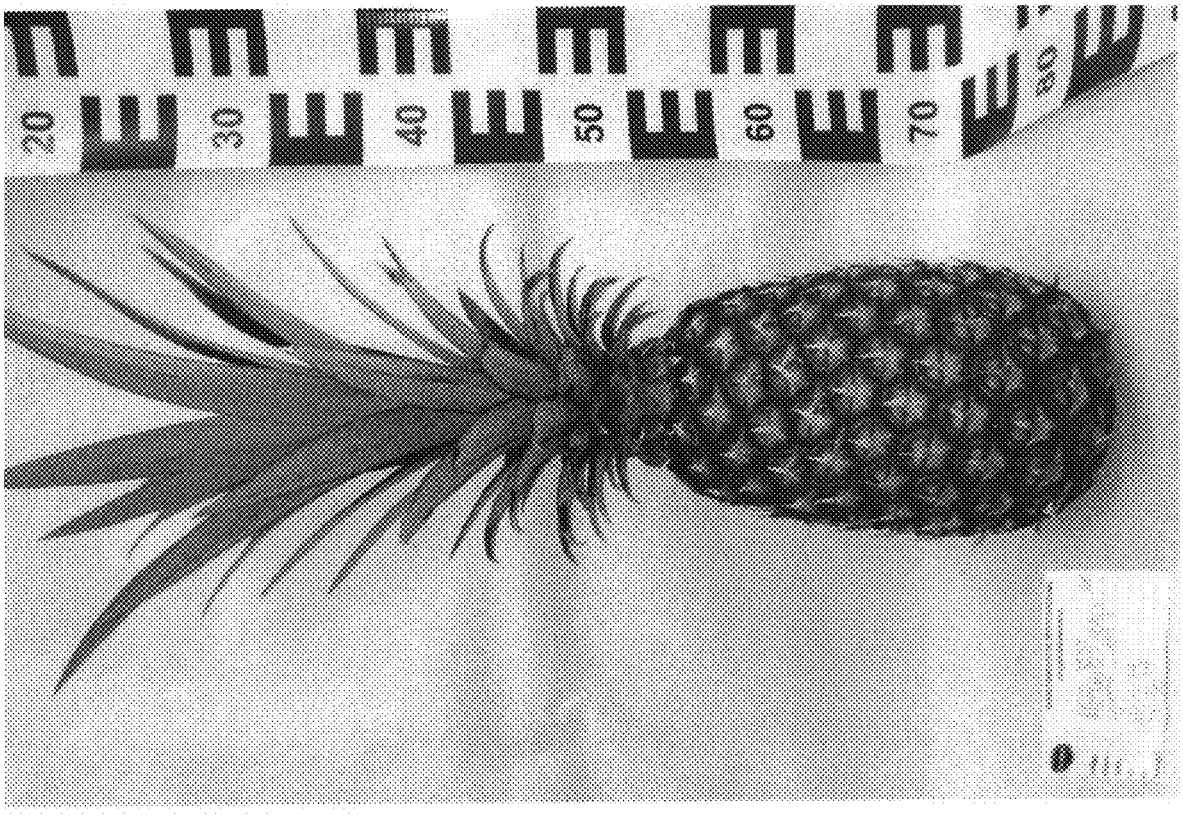

FIG. 5. Shows a close-up of a mature fruit 'Vintage Ruby' at 13.6 months (DP to DoF=8 months+5.6 MAF).

Figure 6:
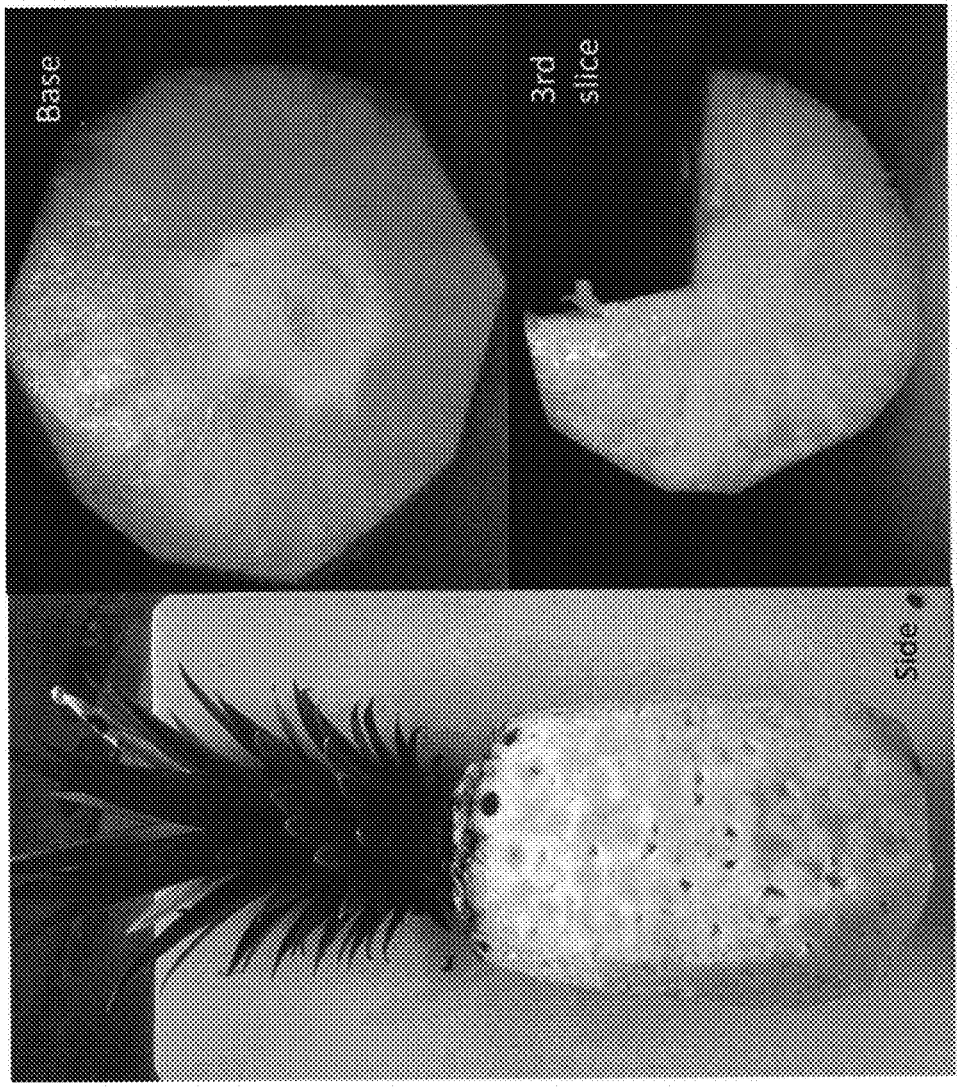

FIG. 6. Shows the internal, lateral and transversal appearance (base and third slice) of harvested fruit at 13.6 months, harvested at fruit external color 4.

The foregoing and other features and advantages of the plant will be apparent from the following detailed botanical description, as illustrated in the accompanying photographs.

DETAILED BOTANICAL DESCRIPTION

The new *Ananus comosus* cultivar 'Vintage Ruby' has not been observed under all possible environmental conditions. However, the plants were grown under environmental conditions and cultural practices which approximate those generally used in commercial pineapple growing operations. The phenotype of the new cultivar may vary depending on the environmental conditions such as temperature, humidity, light intensity and photoperiod without any change made to the genotype of the plant.

The aforementioned photographs, together with the following observations, measurements and values describing plants of 'Vintage Ruby' are based on observations made under optimally fertilized and growing conditions, in the region of Buenos Aires, Puntarenas, Costa Rica (latitude 9.148773° and longitude −83.336024°), a 350 masl, where the temperatures generally range from 14° C. to 37° C., and an annual rainfall average of 3251 mm.

The plants were developed at Buenos Aires-Puntarenas, Costa Rica.

The color terminology and designation reported here are in accordance to the Munsell Color Notation for Plants Tissues published by Munsell Color Macbeth, a division of Kollmorgen Corporation, Baltimore, Md. USA.

The following description was made at the floral induction of the population derived from the F1 hybrid obtained by the leaf crown budding technique and was planted in 2019.

Plant identification: Name: *Ananas comosus* var. *comosus.*

Parental Lines: Selected plant F1 backcrossed with *A. comosus* var. *comosus* 'MD-2'.

Origin: Conventional genetic improvement, through crossing, backcrossing and clonal selection, with a final G2 propagation by vegetative means.

Classification: Botanical: Bromeliaceae or pineapple family. Subfamily: Bromelioidae. Genus: *Ananas*. Subgenus: *comosus*. Variety: 'Vintage Ruby'.

Commercial: Bromeliad fruit plant (pineapple).

Form: Terrestrial (in plantation), with overlapping, sessile leaves from a funnel-formed rosette, surrounding a composite inflorescence (during anthesis), with 0 slips in the fruit peduncle and suckers that are produced in the stem and originate subsequent crops.

General description: 'Vintage Ruby' (before anthesis).

Stem:

I. *General*.—Short, vertical and covered by overlapping leaves, each leaf with a dominant axillary bud.

II. *Stem texture*.—Glabrous and fleshy.

III. *Stem size*.—A) Length (above soil level): usually between 8 and 15.5 cm at anthesis. B) Diameter between 5 and 7.4 cm at ground level to the anthesis.

IV. *Stem shape*.—Cylindrical and with a narrower diameter at the distal part.

V. *Stem color*.—7.5 GY 7/1.

Leaves:

I. *General*.—Closely overlapping sessile leaves (formed in acropetal succession) forming a dense rosette, the outline of which in longitudinal section is roughly heart shaped. The number of leaves fluctuates between 42 and 60 with a 5/13 phyllotaxy.

II. *Texture*.—A) Upper epidermal area: Glabrous, semi-rigid and channeled (or concave) except at the leaf tip. B) Lower epidermal area: Finely striated (longitudinally) and appears covered with a white layer consisting of scale-like trichomes.

III. *Leaf arrangement*.—Alternate and in rosette shape.

IV. *Leaf margins*.—Flat, with rarely found irregularly spaced small deltoid-cuspidate hooked spines usually located on the distal portions of leaves.

V. *Leaf venation*.—Parallel.

VI. *Leaf shape*.—Leaves are not uniform in shape and vary with the position of the leaf on the stem. The basal or oldest leaves are lanceolate while the base is considerably expanded. There is a noticeable narrowing in width between non-chlorophyllous (basal) and chlorophyllous (or main portion) of the leaves. The longest or most mature leaves are lanceolate in shape, but the base is without the arcuate expansions of the preceding leaves. The remaining leaves (or center leaves of the plant rosette) are lanceolate in form with no expansion of width into the base.

VII. *Leaf size* (*to anthesis*).—A) Length: Usually between 64 and 89 cm for those leaves originated from the medium part of the stem with a non-chlorophyllous base that usually is between 2.7 and 6.5 cm in length. B) Width: Normally between 4.9 and 7.8 cm in the mid leaf area of the longest leaves. The expanded basal disk usually has a maximum width of 9.3 to 13.4 cm. C) Thickness: In the longest leaves, it usually varies between 2.34 to 3.55 mm at the center of the mid leaf area and decrease laterally between 1.1 and 1.42 mm at the margin, while becoming slightly thinner towards the tip. The expanded basal disk at the mid stem area usually has a maximum thickness of 2.05 to 3.48 mm at the center of the blade and tapering laterally toward margins up to 0.48 to 0.94 mm. D) Terminal crown leaves: average size 9.4 cm, number 77; and margin type smooth.

VIII. *Leaf color*.—A) Upper epidermal surface: 1. General: dominant color is usually reddish purple, dark purple. The color of the basal disk is predominantly white and light purple. 2. Chlorophyllous basal disk area: commonly pale white 3. Mid leaf area: commonly reddish purple (7.5 R 2/3). 4. Leaf tip area: commonly dark purple (7.5 R 1/6). B)

Lower epidermal surface (underside): 1. General: commonly reddish purple to grayish red with pale white basal disk area. 2. Lower epidermal surface: scaly surface with dark colors, commonly grayish purple (7.5 R 5/2).

Inflorescence (at anthesis):

I. *General*.—Flower composite from 112 to 208 fruitlets borne per inflorescence of a long peduncle of approximately 11 to 17 cm length at the apical meristem. Individual bisexual flowers that consists of three Sepals, Six Stamens, three Stigmas and three Carpels. The inflorescence is self-incompatible producing edible fruit parthenocarpically.

II. *Texture*.—Glabrous and fleshy.

III. *Shape*.—Oval with slightly raised flowers with a light red to grayish red color in the crown.

IV. *Size and color*.—Comparable to specimens of *Ananas comosus* var. *comosus*. Petal size: 1.65 cm. Petal color in the apex: light purple (7.5 P 4/12).

V. *Sepal size*.—0.4-0.6 cm. Sepal color: reddish brown (7.5 R 3/4).

VI. *Floral bract's length*.—From 1.7 to 2.1 cm, serrated margins (with tiny spines); reddish color 5 R 6/14.

Crown:

I. *General*.—Usually one crown. Crown leaves are short and erect to anthesis.

II. *Leaf arrangement*.—Alternate and in rosette shape.

III. *Leaf margins*.—Flat with smooth borders. Seldom very small spines in the tip of one leaf.

IV. *Size*.—Average 24.3 cm. Weight: average 223.5 g.

V. *Shape*.—Medium crown with thin and semi-rigid leaves.

VI. *Color*.—Color of the terminal crown leaves: Reddish color at the apex (7.5R 2/8) and grayish purple at the base (5 GY 8/6).

Fruit (at harvest):

I. *Size*.—Usually with a weight between 1600 and 3300 grams and an average weight of 2477 grams. Fruit core's diameter 3.02 cm.

II. *Shape*.—Cylindrical to slightly conic with flat and medium size fruitlets. Medium crown with thin and semi-rigid leaves. Average fruit's height 15-25 cm, fruit's diameter: average 12.38 cm.

III. *How borne*.—The development of the fruit occurs from the apical meristem of the plant on a long peduncle, usually between 11 and 17 cm length.

IV. *Color*.—A) Shell: commonly red/purple (7.5 R 4/12), with yellowish brown bract (2.5Y 8/8). Fruit peduncle light yellow (10Y 9/10) B) Pulp: Usually yellow (10Y 9/12) to light yellow (10Y 9/10).

V. *Brix*.—Typically, between 12.4 and 15.1 degrees, with an average of 13.77 degrees.

VI. *Total acid levels*.—Usually between 0.26 and 0.91 milligrams of citric acid/ml of juice, with an average of 0.58 mg/ml.

VII. *Vitamin C content reported as ascorbic acid content*.—Regularly between 25.58 and 70.13 mg/100 ml of juice, with an average of 48.78 mg/100 ml.

*Plant/fruit resistance/susceptibility to pest and diseases*.—The plant of the new variety 'Vintage Ruby' performs very similar to 'MD-2'. Table 2 shows the comparison of pineapple varieties 'Vintage Ruby', 'MD-2' and 'Champaka' (not patented) and their resistance to pest and diseases.

Others:

I. *Fertility*.—This plant is self-incompatible. This is the reason why the presence of sexual seeds is almost null. The material used for planting are suckers and fruit crowns.

II. *Vigor*.—This plant has a greater vigor than its parents F1 and 'MD-2'.

III. *Yield*.—A population of this pineapple can have an agronomic yield from 114 to 236 ton/ha.

IV. *Plant use*.—The fruit will be commercialized within the fresh fruit and processed fruit markets.

V. This plant has none or very few (1) suckers.

Summary of the special characteristics of 'Vintage Ruby' hybrid: the plant of 'Vintage Ruby' presents differences compared to its parental lines, such as:

I. Red/purple shell color with yellow pulp: the backcross between F1 and 'MD-2', ended up in a combination of a fruit with bright red/purple shell and yellow pulp similar to 'MD-2'.

II. Plant with absence of slips: 'MD-2' variety produces between 1-3 slips per plant, and the F1 produces between 4-6 slips per plant. By comparison, 'Vintage Ruby' doesn't produce slips at all, which reduces cosmetic and pest problems that can be originated by the contact of the slips with the fruit.

III. The fruit presents suitable levels of brix, citric acid and ascorbic acid similar to 'MD-2' and far superior than the F1. As a result of the backcross process, 'Vintage Ruby' has a red shell color at the time of full maturity, similar to the F1; and with fruit size, pulp color, and internal quality similar to the 'MD-2'. This combination of characteristics is important to differentiate this hybrid from its parents; as shown on Table 3, when reproduced asexually, these characteristics are stable and reproducible for successive generations.

TABLE 1

Average score for select traits of the 'Vintage Ruby' hybrid. 'Vintage Ruby' represents the first plant evaluated when backcrossing 'MD-2' with M01'901 (8-2-24); G1 represents the first asexual propagation of the selected hybrid 'Vintage Ruby'.

| Generation | n | Brix | Ascorbic. Acid (m g/100 ml) | Citric Acid (mg/ml) | Fruit Weight (g) | Number of slips |
|---|---|---|---|---|---|---|
| 'Vintage Ruby' | 1 | 14.6 | 49.1 | 0.70 | 2400 | 0 |
| G1 | 15 | 13.7 | 47.7 | 0.62 | 3039 | 0 |

Individual plant description: The following is an overview of a new pineapple plant variety, that was developed through hybridization process. in Buenos Aires, Puntarenas, Costa Rica.

Plant age: 8 months after planting, and 150 days after forcing.

Plant growth habit: Semi-upright.

Plant diameter: Around 85 cm between opposite leaf tips.

Plant height: 80.78 cm above ground surface.

Stem:

*Length*.—Between 8 and 15.5 cm above ground surface.

*Diameter*.—Between 5 and 7.4 cm above ground surface.

Leaves:

I. *Number*.—57 leaves.

II. *Length*.—77.39 cm the longest leaf.

III. *Width*.—(Largest leaves) at mid leaf (max.) 7.8 cm; at basal disk area (max.) 14.4 cm. Leaf piping is absent.

IV. *Thickness*.—2.8 mm along the axis.

V. *Color* (*from* 5*R* 4/6 *to* 5*RP* 1/1).—A) Upper epidermal area — Chlorophyllous area: Commonly purple and reddish purple (from 5R 3/2 to 5R 1/4). B) Upper epidermal area — Non chlorophyllous area: commonly pale white (5Y 8/1). C) Lower epidermal area: Commonly from reddish purple to grayish purple ((from 5R 9/3 to 7.5 R 5/2). Leaf anthocyanin coloration is strong.

Inflorescence:

General: Composite flower with an inflorescence borne form a long peduncle at the apical meristem. The flower is composed of 136 fruitlets.

Comparison of 'Vintage Ruby' with other pineapple varieties: There are many pineapple varieties growing worldwide; most varieties are grown for local consumption, very few are grown for international commercialization and market distribution. 'Vintage Ruby' could be cultivated for exporting to United States, Europe, and other countries. Most of the comparison data were generated to contrast with 'MD-2' and 'Morada'.

I. *Petals*.—The following describes the width and texture of the Petals.

| | ID UPOV | Trait | Note |
|---|---|---|---|
| Inflorescence | 14 | Size of bracts (cm) | 1.9 ± 0.2 |
| | 15 | Petal: color of apex (purple red), base (white) | 2 |
| | 16 | Petal length (mm) | 23.4 ± 0.3 |
| | N/A | Petal width (cm) | 6.38 ± 0.4 |
| | N/A | Petal Height | 1.56 ± 0.3 |
| | N/A | Petal texture | very finely textured and feel smooth |

II. *Reproductive organs*.—The following describes the characteristics of the reproductive organs.

| | Trait | |
|---|---|---|
| Inflorescence | Stigma (mm) | 1.4 ± 0.36 |
| | Style (mm) | 16.9 ± 1.07 |
| | Ovary (mm) | 9.2 ± 1.02 |
| | Stamen (mm) | 13.15 ± 1.17 |
| | Anther length (mm) | 4.6 ± 0.4 |
| | Pollen (μm) | 6.5 |
| | Stigma shape | rounded |
| | Style shape | tubular |
| | Ovary shape | round |
| | Stamen shape | tubular |
| | Anther shape | Bilobed introrse |
| | Pollen shape | oval |
| | Stigma color | From 7.5P 9/3 to 7.5P 6/10 |
| | Style color | Base = white, top = pale purple |
| | Ovary color | White/pale yellowish |
| | Filament color | Filament base = white, filament top = pale purple |
| | Anther color | Pale yellow |
| | Pollen color | transparent |

III. *Peduncle*.—The length and diameter of the peduncle are as follows.

| Peduncle | ID UPOV | Trait | Note |
|---|---|---|---|
| | 21 | Length (cm) | 14.6 ± 1.7 |
| | 22 | Diameter (cm) | 3.0 ± 0.6 |

Table 2. depicts differences in susceptibility to pest and diseases: 'Vintage Ruby' and 'Champaka' are less susceptible than 'MD-2' to *Thielaviopsis* sp. (common fruit rot) and 'Vintage Ruby' and 'MD-2' are similar in their susceptibility to *Elaphria* sp. (a moth species).

TABLE 2

Susceptibility to pest and diseases of different commercial varieties.

| | Pineapple Variety | | |
|---|---|---|---|
| Pest/Disease | 'Vintage Ruby' | 'MD-2' | 'Champaka' |
| *Elaphria* sp. | S+ | S+ | S |
| Mealybug (*Dysmicocus brevipes*) | S | S | S |
| Thecla (*Strymon* spp) | S | S | S |
| *Thielaviopsis paradoxa* (TV) | S | S+ | S |
| *Phytophtora parasitica* | S | S | S |
| *Helicotylenchus* sp. | S | S | S |
| *Heloidogyne* sp. | S | S | S |
| *Pratylenchus* sp. | S | S | S |

The pineapple variety 'Vintage Ruby' has a post-harvest shelf life similar to 'MD-2', showing similar performance in shell dehydration studies.

'Vintage Ruby' characteristics differ from other varieties in the following aspects. General characteristics of the fruit are as follows (A) a fruitlet apex which is flat; (B) the flesh density is medium; (C) the number pf fruitlets per syncarp is 120-140; (d) the fruitlet characteristics are as follows:

| | ID UPOV | Trait | Note |
|---|---|---|---|
| Fruit | 31 | Fruit shape (Medium ovate) | 2 |
| | 32 | Fruit length (cm) | 19.8 ± 6.7 |
| | 33 | Fruit diameter (cm) | 11.5 ± 3.4 |
| | 34 | Predominant color of mature eye (red) | 9 |
| | 35 | Fruit: Size (medium) | 5 |
| | N/A | Size of eye diameter width (cm) | 2.1 ± 0.7 |
| | N/A | Size of eye length (cm) | 2.7 ± 0.3 |
| | N/A | Color of immature eye (Deep purple) | 6 |
| | 37 | Fruitlet apex (flat) | 2 |
| | 38 | Evenness of color of eyes (even or slightly uneven) | 1 |

I. *Shell color*.—Its shell color at mature and immature stages is similar to the 'Morada' variety.

II. *Weight and shape of fruit*.—'Vintage Ruby' fruit weight is significantly greater than 'Morada's', and similar to the 'MD-2', and 'Champaka', with a cylindrical to slightly conical fruit shape.

III. *Ascorbic acid*.—'Vintage Ruby' has a higher content of ascorbic acid than its relative *A. comosus* cv. 'Morada', but similar to 'MD-2' and 'CO-2'.

IV. *Citric acid*.—'Vintage Ruby' citric acid content is similar to 'MD-2'.

V. *Brix*.—The sugar content (measured as brix degrees) of 'Vintage Ruby' is similar to that found on 'MD-2', higher than 'Singapore Spanish' and somewhat lower to 'Josephine' variety.

VI. *Age to forcing*.—'Vintage Ruby' is vigorous and can reach forcing plant size 7 to 8 months after planting. Although this depends on the planting material used and the desired plant weight for floral induction, under similar conditions, 'MD-2' which reaches an optimal forcing size 8.5 months after planting.

VII. *Leaf spines*.—This characteristic is commonly used to differentiate pineapple plants from other varieties. The color of the leaf spines are as follows: Tip: pale yellow 10Y 9/1, base: pale red 2.5R 3/8. 'Vintage Ruby' does not have conspicuous or regular thorns on the leaf like its parental 'Morada'. It does have inconspicuous thorns at the leaf tips, like its parental 'MD-2', although 'MD-2' often presents irregular thorns on the edges of the leaf blade as well.

Table 3 compares some of the most important characteristics for fresh fruit versus local varieties for exportation. This chart shows comparisons between 'Vintage Ruby' and other varieties.

TABLE 3

Comparative characteristics of different pineapple varieties and cultivars

| Variety/ | Number of slips | Fruit weight (g) | | Ascorbic Acid (mg/100 ml) | |
|---|---|---|---|---|---|
| Cultivar[10] | Average | Range | Average | Range | Average |
| 'Vintage Ruby' | 0 | 0 | 2477 | 1600-3300 | 48.78 |
| 'MD-2'[1] | 1.2 | 0-3 | 1820 | 1070-2560 | 53.06 |
| 'Morada'[2] | 7.57 | 4-9 | 1887 | 1566-2000 | 20.3 |
| 'Honey Gold' | 1.5 | 0-3 | 1033 | 450-1678 | 21.14 |
| 'Champaka 153'[2] | 1.1 | | 1710 | 420-3010 | 12.91 |
| 'Champaka F152' | 1.5 | | 2328 | | |
| 'CO-2'[3] | | 2-3 | 2059 | 1297-2590 | |
| 'Singapore Spanish'[4] | | 2-12 | 1000 | | |
| 'Sarawak'[4] | 0 | | | 2000-4000 | |
| 'Mauritius'[4] | 0 | | | 500-1500 | |
| 'Josephine'[5] | | | | 1100-1300 | |
| 'Scarlett'[5] | | | | 1400-2000 | |
| 'Red Spanish'[5] | | 1-3 | | 1200-2000 | |
| 'T'ainung 11'[6] | 6.9 | | 991 | 733-1269 | |
| 'Imperial'[7] | 9 | | 1792 | | |
| 'Perolera'[7] | | 8-10 | 1800 | | |
| 'Pemambuco'[8] | | | | 1000-1500 | |
| 'Primavera'[8] | | 7-10 | 1300 | | |
| 'Queen'[9] | 10 | | | 500-1000 | 26 |

TABLE 3-continued

Comparative characteristics of different pineapple varieties and cultivars

| Variety/ | Citric Acid (mg/ml) | | Brix (+20 ) | | |
|---|---|---|---|---|---|
| Cultivar[10] | Range | Average | Range | Average | Range |
| 'Vintage Ruby' | 25.58-70.13 | 0.58 | 0.26-0.91 | 13.77 | 12.4-15.1 |
| 'MD-2'[1] | 37-69.06 | 0.6 | 0.36-0.84 | 15.05 | 12.9-17.2 |
| 'Morada'[2] | 9.9-24.9 | 0.69 | 0.58-0.86 | 13.51 | 12.2-15.1 |
| 'Honey Gold' | 14.73-37.36 | 0.98 | 0.67-1.33 | 16.18 | 14.4-18.1 |
| 'Champaka 153'[2] | 8.10-17.72 | 0.72 | 0.54-0.90 | 14.33 | 11.6-17.0 |
| 'Champaka F152' | | 0.73 | | 14.97 | |
| 'CO-2'[3] | 30.8-55.50 | | 0.42-0.91 | | 15.0-16.7 |
| 'Singapore Spanish'[4] | | | 0.50-0.60 | | 10.0-12.0 |
| 'Sarawak'[4] | | | 0.30-0.65 | | 14.0-17.0 |
| 'Mauritius'[4] | | | 0.40-0.60 | | 15.0-17.0 |
| 'Josephine'[5] | | | | | 17.0-22.0 |
| 'Scarlett'[5] | | | | | 15.0-18.0 |
| 'Red Spanish'[5] | | | | 12 | |
| 'T'ainung 11'[6] | 1.40-18.50 | 0.5 | 0.40-0.60 | 14 | 13.2-15.1 |
| 'Imperial'[7] | | 0.62 | | 15.8 | |
| 'Perolera'[7] | | 0.64 | | 13.1 | 14.0-16.0 |
| 'Pemambuco'[8] | | | | | |
| 'Primavera'[8] | | 0.51 | | 13 | |
| 'Queen'[9] | | 0.56 | | | 14.0-16.0 |

[1]Pindeco's historical data base and monthly research report April 2001.
[2]Pindeco's fruit historical data base. Pindeco's forcing plant weight data base.
[3]Plant patent 8,863.
[4]Wee, Y. C. 1972. Some common pineapple cultivars of west Malaysia. Malays Pineapple pp 7-13.
[5]Bartholomew et al. 2003 The Pineapple, Botany, Production and Uses.
[6]Chang, Ching-Chyn, 1995 Tainung No. 13. Pineapple. Jour. Agric. Res. China 44(2): 287-296.
[7]Pinto da Cunha et al. O abacaxizeiro. Pineapple News Issue No 10 May 2003.
[8]Pinto da Cunha et al. O abacaxizeiro. Py et al. The pineapple Cultivation and uses.
[9]Del Monte pineapple germplasm collection database.
[10]Cultivars are unpatented unless indicated otherwise.

Literature: Munsell Color chart for Plant Tissues. Google Play. Android App. 2017.

What is claimed is:

1. A new and distinct *Ananas comosus* plant named 'Vintage Ruby', as illustrated and described herein.

* * * * *